United States Patent [19]

Otsuji et al.

[11] Patent Number: 5,166,196
[45] Date of Patent: Nov. 24, 1992

[54] METHOD FOR REMOVING IMMUNOCOMPLEXES FROM BLOOD

[75] Inventors: Kazuya Otsuji; Hakaru Inaoka, both of Utsunomiya; Yasuki Honda, Ichikai; Kikuhiko Okamoto, Koshigaya; Morihisa Tanaka, Tokyo; Tsukasa Matsumoto, Tokyo; Koji Ijima, Tokyo; Jong-Chol Cyong, Tokyo, all of Japan

[73] Assignee: Kao Corporation, Tokyo, Japan

[21] Appl. No.: 860,590

[22] Filed: Mar. 30, 1992

Related U.S. Application Data

[63] Continuation of Ser. No. 521,380, May 10, 1990, abandoned.

[30] Foreign Application Priority Data

May 12, 1989 [JP] Japan .................... 1-119645

[51] Int. Cl.$^5$ .............. A61K 31/725; C08B 37/00; C12S 3/14
[52] U.S. Cl. ............................ 514/54; 536/123; 530/413
[58] Field of Search .................. 514/54; 536/123; 530/413

[56] References Cited

U.S. PATENT DOCUMENTS

| | | | |
|---|---|---|---|
| 3,418,311 | 12/1968 | Sakai et al. | 536/123 |
| 4,304,906 | 12/1981 | Kang et al. | 536/123 |
| 4,511,559 | 4/1985 | Szendrei et al. | 536/123 |
| 4,923,809 | 5/1990 | Otsuji et al. | 536/123 |

FOREIGN PATENT DOCUMENTS

| | | | |
|---|---|---|---|
| 0285829 | 12/1988 | European Pat. Off. | |
| 59-11302 | 1/1984 | Japan | 536/123 |
| 61-183301 | 8/1986 | Japan | 536/123 |
| 2079150 | 1/1982 | United Kingdom | 514/54 |

OTHER PUBLICATIONS

Patent Abstracts of Japan, vol. 12, No. 326 (C-525) [3173], Sep. 5, 1988, p. 55; & JP-A-63 090 505 (Tsumura Juntendo, Inc.) Apr. 4, 1988.
Chirkina et al.; Chemical Abstracts 78:553105 (1973).
Mori et al.; Carbohydrate Research 91:49-58 (1981).
J. Biological Chemistry 257(7):3352-3354 (1982).
Gowda et al.; Carbohydrate Research 113:113-124 (1983).
Akiyama et al.; Agric. Biol. Chem. 48(2):403-407 (1984).
Okamura et al.; Chemical Abstracts 112:185577r; 185578s (1990).

*Primary Examiner*—Ronald W. Griffin
*Assistant Examiner*—Nancy S. Carson
*Attorney, Agent, or Firm*—Oblon, Spivak, McClelland, Maier & Neustadt

[57] ABSTRACT

A composition for curing autoimmune diseases is disclosed. The composition comprises as an effective component an acidic heteropolysaccharide which is secreted by a callus induced from a plant belonging to the genus *Polianthes L.* The acidic heteropolysaccharide can be prepared as a uniform product by the application of plant tissue culture methods and exhibits superior capability of removing immunocomplexes with the least side effects.

2 Claims, 3 Drawing Sheets

METHOD FOR REMOVING IMMUNOCOMPLEXES FROM BLOOD

This application is a continuation of application Ser. No. 07/521,380, filed on May 10, 1990, now abandoned.

BACKGROUND OF THE INVENTION

1. Field of the Invention

This invention relates to a composition for curing autoimmune diseases, and, more particularly, to a composition for curing autoimmune diseases possessing superior capability of removing immunocomplexes and exhibiting the least side effects.

2. Description of the Background Art

Researches directed to immunology have achieved a great advance in recent years. Causes and mechanisms of a number of diseases which have been heretofore veiled became elucidated in line with the advance in immunology. Immunological approaches, e.g. immunostimulant, immunosuppressant, etc., are being adopted for curing many of these diseases. For example, in the research of the cancer chemotherapy, certain polysaccharides derived from Basidiomycetesin were found to possess carcinostatic activity and some of them have been placed in actual use. Mechanisms of their carcinostatic activities have also been studied on some polysaccharides, mainly on lentinane derived form shiitake mushroom. Such studies are clarifying their carcinostatic activities through the immunological system.

Along with the studies on polysaccharides as carcinostatic agents, the studies directed to their immunocomplex removal capabilities are undertaken. Immunocomplexes are produced as a result of biological immunoresponse and usually discharged from the reticuloendothelial system via complements or macrophages. In the event that immunocomplexes cannot be discharged for some reason, they accumulate in many organs and cause disorders in cells due to the allergy type III reaction. Glomerular nephritis, articular rhumatism, systemic lupus erythematosus, vascular diseases, and the like are the diseases caused by such disorders. They are intractable and termed autoimmune diseases. No established therapy nor medicament for curing these diseases exist at the present time.

Currently available medicaments administered clinics in an effort to cure autoimmune diseases lack any sufficient therapeutic effects. For example, steroids are used for chronic glomerular nephritis. They do not lead to complete cure of the disease and do not necessarily bring about good results because of their side effects. Also, several immunostimulants are used for the therapy of chronic articular rhumatism, but are also not always satisfactory because of side effects.

In view of this situation, the present inventors have conducted extensive studies in order to develop medicaments which are truly effective to autoimmune diseases without side effects, and found that specific acid heteropolysaccharides possessed remarkable immunocomplex removing activity. The finding has led to the completion of the present invention.

SUMMARY OF THE INVENTION

Accordingly, an object of this invention is to provide a composition for curing autoimmune diseases comprising, as an effective component, an acidic heteropolysaccharide which is secreted by a callus induced from a plant belonging to the genus Polianthes L..

In a preferred embodiment of the present invention said acidic heteropolysaccharide is that comprising arabinose, mannose, galactose, glucuronic acid, and xylose as its structural units, with the following sequence and in the following ratio:

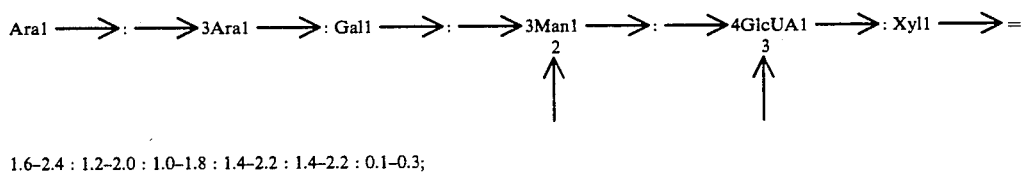

1.6–2.4 : 1.2–2.0 : 1.0–1.8 : 1.4–2.2 : 1.4–2.2 : 0.1–0.3;

and having a molecular weight of $1 \times 10^4 - 2 \times 10^7$.

Other and further objects, features, and advantages of the invention will appear more fully from the following description.

DETAILED OF THE INVENTION AND PREFERRED EMBODIMENTS

Figure 1:
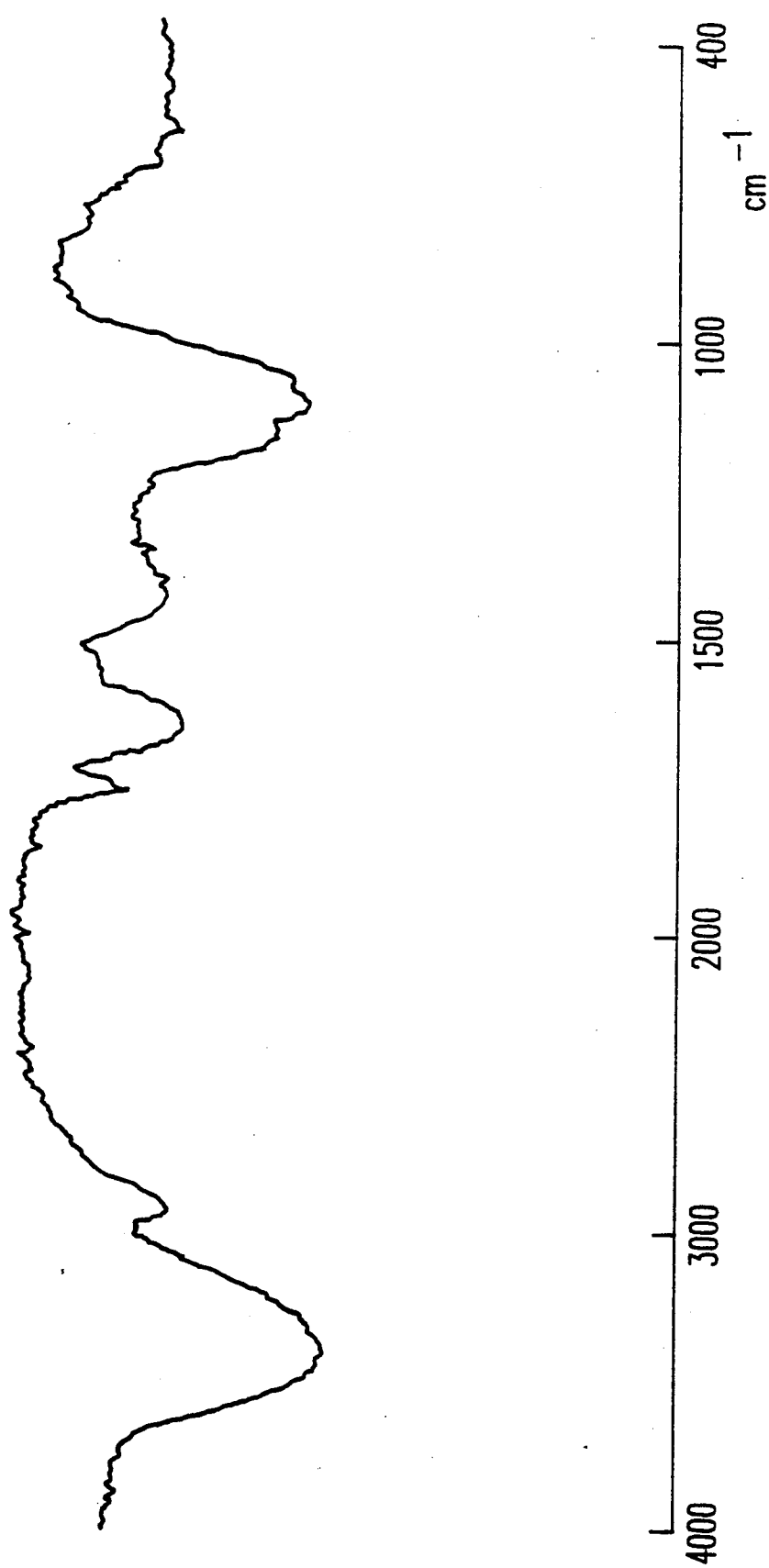
FIG. 1 is a drawing showing infrared spectrum of an acidic heteropolysaccharide which is used as an effective component in the composition of the present invention.

An acidic heteropolysaccharide which is the effective component of the composition of the present invention can be prepared, for example, by culturing a callus induced from a plant belonging to Polianthese L. in a culture medium and collecting the polysaccharide from the culture broth.

A typical example of the plant belonging to Polianthes L. is *Polianthes tuberosa L.* Portions of organs or tissues of the plant such as flowers, stems, leaves, bulbs, roots, or the like are used as the explant. Of these, the most desirable portion is a certain tissue of the flower.

Basal media employed for inducing the callus may be those conventionally employed in plant-tissue culture, and include Murasige-Skoog medium, Linsmaier-Skoog medium, Gamborg medium, White medium, Tuleeke medium, Nitsch & Nitsch medium, or the like.

It is necessary that one or more plant hormones be added to these media. Examples of plant hormones to be employed are auxins such as 2,4-dichlorophenoxyacetic acid (2,4-D), α-naphthaleneacetic acid (NAA), indoleacetic acid (IAA), and indolebutylic acid (IBA); cytokinins such as furfurylaminopurine (kinetin), benzyladenine (BA), and dimethylallylaminopurine (2iP); and the like. Good results are obtained by the independent use of 2,4-D, or the combined use of NAA and BA, or NAA and kinetin. Concentrations of hormones required for inducing the callus are $5 \times 10^{-4}$ to $1 \times 10^{-7}M$ for 2,4-D, when it is employed independently, and $5\times10^{-4}$ to $1\times10^{-7}$M for NAA, when employed in combination with BA or kinetin, wherein BA and kinetin are used at a concentration of $1\times10^{-7}$.

In addition to the basal medium and the plant hormones, sugars are added to the culture medium as a carbon source for inducing the callus. Sugars that can be employed for this purpose include glucose, fructose, mannose, xylose, sucrose, rhamnose, fucose, starch, and the like. Among these, the most typically used sugar is sucrose.

Although either a solid or liquid culture medium can be employed for inducing the callus, the usually employed medium is a solid culture medium.

The callus thus induced can be subcultured over more than 10 generations, while maintaining the same form in the same medium in which it was originally induced. Culture media employed for subculturing are those containing Linsmaier-Skoog medium or Murasige-Skoog medium as a basal medium; 2,4-D at a concentration of $1\times10^{-4}$ to $1\times10^{-7}$M, or a combination of NAA and BA, both at a concentration of $1\times10^{-4}$ to $1\times10^{-7}$M as plant hormones; and glucose, fructose, mannose, xylose, sucrose, rhamnose, fucose, starch, or the like, most desirably, sucrose, at 1 to 6% by weight based on the culture medium, as a carbon source.

For the production of polysaccharides from the callus, the callus is cultured in a solid medium such as an agar medium or in a liquid medium. Culturing in a liquid medium is generally more desirable. The same media used for the culture of callus can be used as a basal medium.

The kind and concentration of the plant hormones have considerable relationship with the productivity of the polysaccharides. The kinds of the plant hormones employed are auxins such as 2,4-D, NAA, IAA, and IBA; cytokinins such as kinetin, BA and 2iP; and gibberellins such as gibberellin $A_3$ ($GA_3$). Among these, the independent use of 2,4-D or NAA, or the use of NAA and BA or kinetin in combination is desirable for obtaining better results. The concentration of hormones is, $5\times10^{-4}$ to $1\times10^{-7}$M, preferably $5\times10^{-5}$ to $5\times10^{-6}$M for the independent use of 2,4-D or NAA, and for the combined use of NAA and BA or kinetin, the NAA's concentration of $1\times10^{-4}$ to $1\times10^{-7}$M, preferably $1\times10^{-4}$ to $5\times10^{-6}$M, and the concentration of BA or kinetin of $5\times10^{-5}$ to $1\times10^{9}$M, preferably $1\times10^{-5}$ to $1\times10^{-7}$M, are used.

Glucose, fructose, mannose, xylose, sucrose, rhamnose, fucose, starch, or the like, is used as a carbon source. The kind of carbon source employed does not have a great effect on the production of the polysaccharides. Sucrose is most usually used. Although there is no significant relationship between the concentration of the carbon source and the amount of polysaccharides produced, a generally desirable concentration of the carbon source is 1 to 6%.

There is no specific limitation to the culture conditions. It is usually desirable, however, to carry out the culture by a shake method at a temperature of 20° to 30° C. for 15 to 30 days.

Polysaccharides are collected from the culture broth thus obtained by subjecting it to centrifugation or filtration to separate the cells therefrom, and by concentrating using a rotary evaporator or the like. Ethanol is added to the concentrate to obtain precipitate, which is then freeze-dried to give crude polysaccharides.

The polysaccharides precipitate thus prepared is purified by a method conventionally utilized for purifying a polysaccharide. For example, the crude polysaccharides are dissolved in water, centrifuged to completely eliminate the insoluble portions, and then subjected to dialysis, or ion-exchange, thus obtaining highly purified polysaccharides.

The purified polysaccharides thus prepared contain novel heteropolysaccharides. When the purified polysaccharides are hydrolyzed using 2N $H_2SO_4$ aqueous solution at 100° C. for 8 hours, subjected to thin-layer chromatography using an eluent of ethyl acetate/pyrimidine/acetic acid/water at a ratio of 5:5:1:3, and colored with an aniline/diphenylamine/acetone/phosphoric acid reagent, arabinose, mannose, galactose, glucuronic acid, and xylose are detected. Analysis of this polysaccharide by gas chromatography also confirmed their existence as constituent sugars. Gas chromatography analysis of this polysaccharide after methylation by the Hakomori method revealed that the substance had the following sequence of combination in the following ratio of each component:

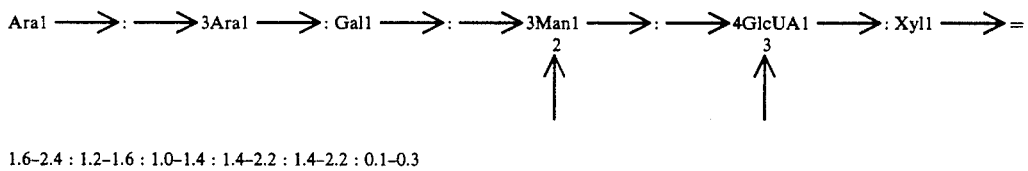

1.6–2.4 : 1.2–1.6 : 1.0–1.4 : 1.4–2.2 : 1.4–2.2 : 0.1–0.3

Also, it was found that 0 to 50% of the carboxylic group of glucronic acid was present as a methyl ester. In addition, the polysaccharides of this invention are identified as acidic in nature because of their absorption by cation-exchange resins. Analysis by high performance liquid chromatography using TSK Gel 4000PW, 5000PW, and 6000PW column (Tradenames, manufactured by Toyo Soda Co., Ltd.) proved that the molecular weight of this substance was $1.0\times10^4$ to $2.0\times10^7$.

The acidic heteropolysaccharides have the following physicochemical characteristics.

Solubility:

Soluble in water, and insoluble in ethanol, ether, and acetone.

Color Reaction:

Anthrone reaction: positive

Carbazole reaction: positive

Erson-Morgan's reaction: negative

Color and Form:

Those precipitated from ethanol are white or gray-white powder. Those purified by dialysis, ion-exchange, and freeze-dried are white in color and cotton-like or fibrous in form.

Specific rotation:

$[\alpha]_D^{25}$: 0 to +20 (C = 1.0 in an aqueous solution)

Figure 2:
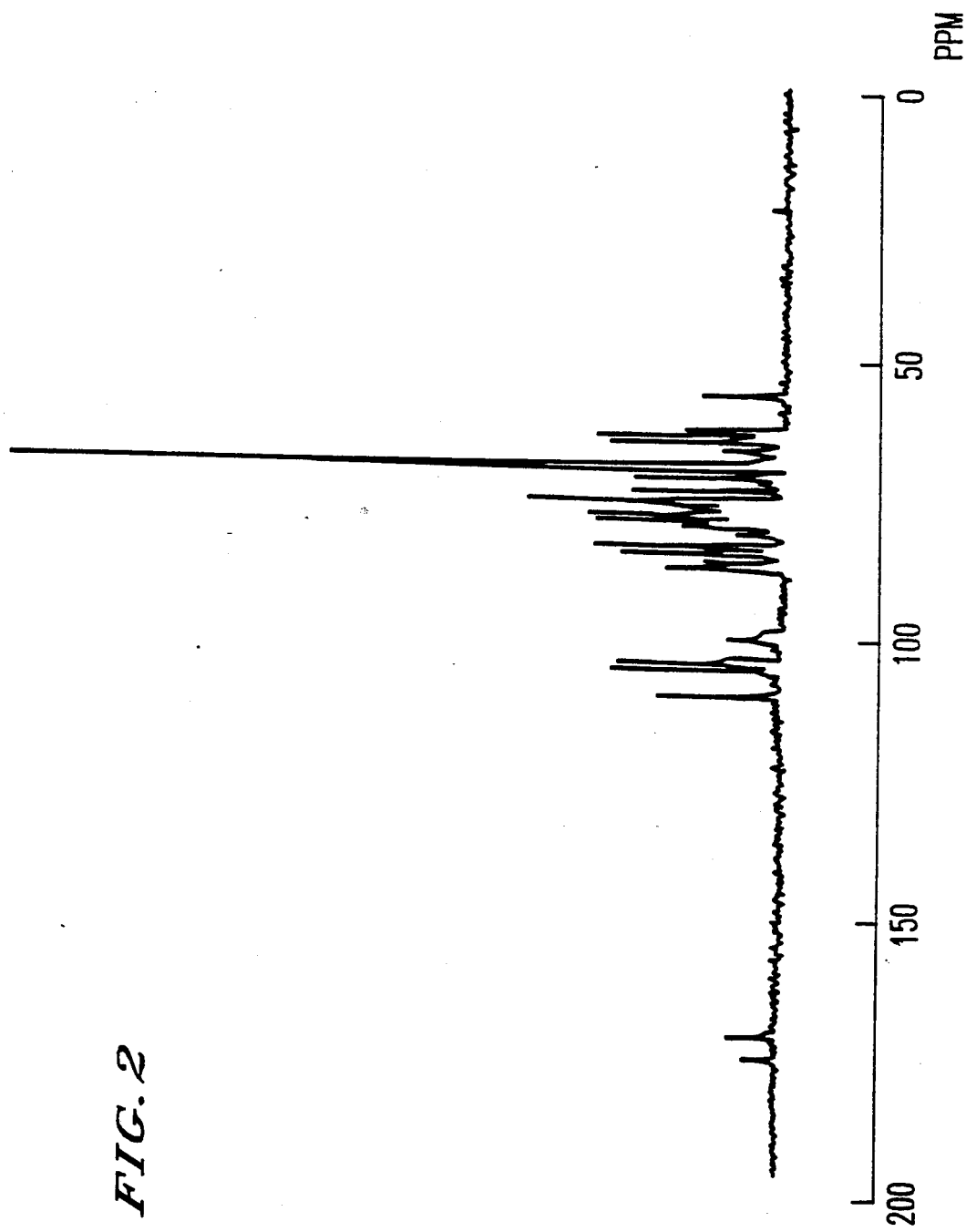
FIG. 2 is a drawing showing $^{13}C$ NMR spectrum of the same substance.

Infrared Spectrum:

Shown in FIG. 1.
NMR Spectrum:
13C NMR spectrum is shown in FIG. 2 (eluent: D₂O; tube: 5 mm; internal standard: dioxane).

The acidic heteropolysaccharides of this invention have the following recurring unit:

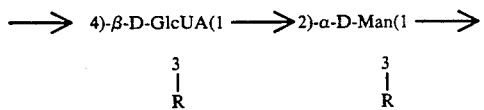

wherein R is:

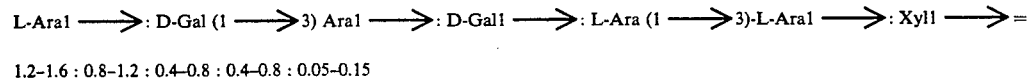

1.2–1.6 : 0.8–1.2 : 0.4–0.8 : 0.4–0.8 : 0.05–0.15

As described in Japanese Patent Application Laid-open No. 10997/1989, the acidic heteropolysaccharides of this invention are novel in the art from their comparison with other polysaccharides. Specifically, there are known polysaccharides in the art which have as a partial unit the glucuronomannan structure [→2)-α-D-Man-(1→4)-β-D-GlcUA-(1→], contained in the acidic heteropolysaccharides of this invention. These polysaccharides are obtained from *Drosera capensis* (Channe et al., *Carbohydr. Res.*, 113, 113-124, 1983), from *Drosera binata* (Channe et al., *Phytochemistry*, vol. 21, No. 9, 2297-2300, 1982), and from culture cells of *Nicotiana tabacum* (Mori et al., *Carbohydr. Res.* 91, 49-58, 1981; Akiyama et al, *Agric. Biol. Chem.*, vol. 48, No. 2, 403-407, 1984), etc. Polysaccharides obtained from *Drosera capensis* and *Drosera binata*, however, are clearly different from acidic heteropolysaccharides of this invention in that they have —2Man1— and —4GlcUA1— as their major bonds, and do not have —3Ara1—. The polysaccharide obtained from *Nicotiana tabacum* is also clearly different from the acidic heteropolysaccharides of this invention. Specifically, it does not have the —3Ara1— bond as its major bond, according to the report by Mori et al; and according to the report by Akiyama et al., it has —4GlcUA1—, —2-Man1—, and —5Ara1— as its major bonds, and again, does not have —3Ara—1. The acidic heteropolysaccharides used as an effective component in the composition of this invention are therefore novel polysaccharides which are different from any other polysaccharides conventionally known in the art.

The above acidic heteropolysaccharides are water soluble and can be administered by injection dissolved into physiological saline. Alternatively, they can be mixed with carriers such as kaolin, talc, lactose, starch, microcrystalline cellulose, and the like, and prepared into such preparations as tablets, powders, granules, capsules, and the like for oral administration.

A preferable dose is, for adult man, 1 to 20 mg in a week and 1 to 10 mg at one time, when it is injected, and 10 to 200 mg in a week and 10 to 100 mg at one time, when orally administered.

Since the composition of this invention possesses a superior immunocomplex removal capability with the least side effects, it is very effective for curing autoimmune diseases. The polysaccharides which are the essential component of the composition can be prepared as a uniform product by the application of plant tissue culture methods.

Other features of the invention will become apparent in the course of the following description of the exemplary embodiments which are given for illustration of the invention and are not intended to be limiting thereof.

EXAMPLES

EXAMPLE 1

Preparation of Polysaccharides

*Polianthes tuberosa L.* was selected as a plant belonging to the genus Polianthes L. Callus was induced by culturing a bud of tuberose 2 to 7 days before blooming in a Linsmaier-Skoog medium (agar medium) containing $1 \times 10^{-5}$M NAA and $1 \times 10^{-6}$M BA as plant hormones and 3% of sucrose as a carbon source. The induced callus was subcultured in the same culture medium for several generations. The subcultured and stabilized callus was inoculated at a concentration of 5% into a Linsmaier-Skoog medium (liquid medium) containing 2,4-D at a concentration of $1 \times 10^{-5}$M and 5% of sucrose as a carbon source. The callus was shake-cultured in a rotary shaker at a rotation of 120 rpm and at $27° \pm 1°$ C. for 30 days. Cells were removed from the culture broth by filtration and centrifugation, and the filtrate was concentrated by a rotary evaporator. To this concentrate was added 3-fold in volume of ethanol, and the mixture was allowed to stand at 5° C. for 24 hours to obtain a precipitate, which was collected by means of centrifugation, washed three times with 70% ethanol, and freeze-dried to remove the water therefrom, thus obtaining the target polysaccharide.

The above procedure was repeated 5 times in total. Variations between the lots in the polysaccharide yield, total saccharide amount, uronic acid content, protein content, water content, and neutral sugar composition were determined. The results are shown in Table 1.

TABLE 1

| Lot No. | Polysaccharide yield (g/l) | Total saccharide amount (%) | Uronic acid content (%) | Protein content (%) | Water content (%) | Neutral sugar composition* | | | |
|---|---|---|---|---|---|---|---|---|---|
| | | | | | | Ara | Xyl | Man | Gal |
| I | 3.22 | 95.3 | 21.4 | 1.8 | 1.3 | 10 | 0.7 | 6.7 | 6.8 |
| II | 3.01 | 96.0 | 20.4 | 1.5 | 0.9 | 10 | 0.6 | 6.5 | 7.1 |
| III | 2.89 | 93.2 | 19.0 | 1.7 | 2.0 | 10 | 0.9 | 6.6 | 6.9 |
| IV | 3.30 | 95.5 | 18.9 | 1.7 | 1.7 | 10 | 1.0 | 6.7 | 7.0 |
| V | 3.02 | 94.0 | 22.7 | 1.6 | 2.1 | 10 | 0.7 | 6.6 | 7.2 |

*Proportion of Xyl, Man, and Gal when the amount of Ara was taken as 10.

As evident from Table 1, the polysaccharide produced by the above method which is completely artificially controlled is very uniform with the least fluctuations between lots in the polysaccharide yield, total saccharide amount, uronic acid content, protein content, water content, and neutral sugar composition.

EXAMPLE 2

In Vitro Immunocomplex Removal Test (a) Preparation of Macrophage

A thioglycolate medium was intraperitoneally injected to a mouse (age: 7–8 weeks). After 96 hours, peritoneal exudate cells (PEC) were collected by washing with purified physiological saline. The PEC was adjusted to a concentration of $1 \times 10^6$ cell/ml in a PRMI1641 medium containing 10% fatal calf serum (FCS). A 100 µl aliquot of the solution was charged into each hole of a 96-hole microplate and cultured at 37° C. for 2 hours in a 5% $CO_2$ atmosphere. Cells not adhered to the holes were removed by washing with a phosphate buffer solution (PBS). 200 µl of the PRMI1641 medium containing 10% of FCS was added to the holes and the culture was continued under the same conditions. Cells adhered to the plate was served as macrophage.

(b) Culture with Acidic Heteropolysaccharide

Acidic heteropolysaccharide prepared in Example 1 was concentration of 1,000 µg/ml and the solution was served as a sample. The sample was added to the macrophage culture broth to a final concentration of 91 µg/ml and was cultured for 15 hours.

(c) Determination of Immunocomplex Bonding Capacity by In Vitro EIC Assay

Mouse glucose oxidase anti-glucose oxidase complex (GAG) purified by gel filtration was added to the macrophage cultured in (b) above as an immunocomplex, and allowed to stand at 4° C. to combine it with the macrophage. Holes were washed to remove uncombined GAG with the macrophage. The amount of GAG combined with the macrophage was determined by coloring the sample using ABTS as a substrate in the presence of surplus glucose and peroxidase, followed by measurement of absorbance at 405 nm. LPS derived from E. coli was used as a positive control. The results are shown in FIG. 3.

Figure 3:
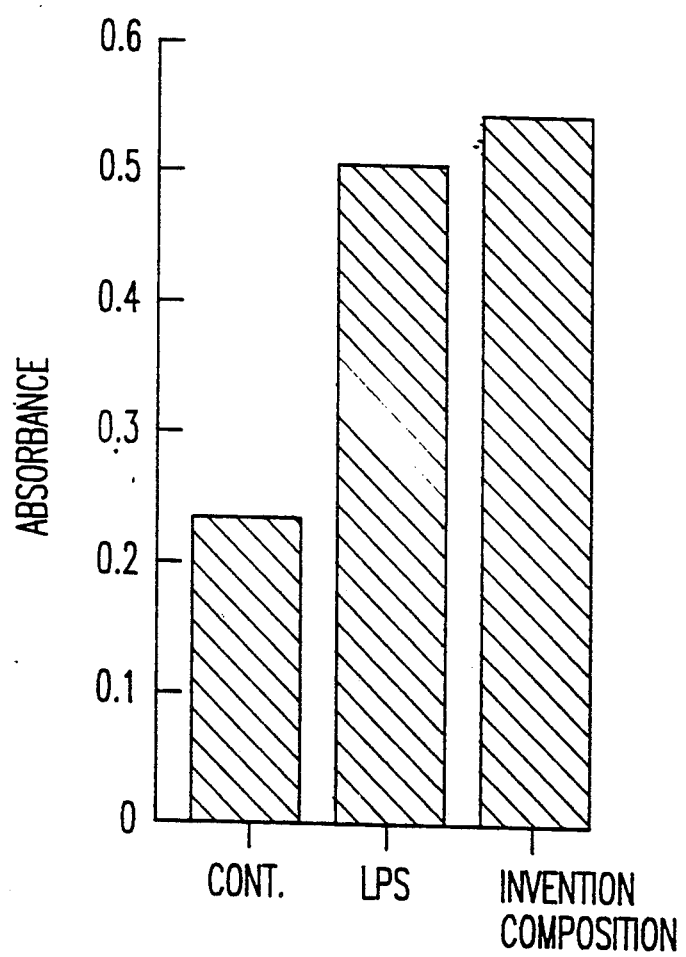
FIG. 3 is a drawing showing the increase in the immunocomplex bonding capacity by the use of the composition of the present invention.

As evident from FIG. 3, the macrophage cultured by the polysaccharide exhibited a remarkable increase in its bonding capacity with GAG (an immunocomplex). The result was equivalent to or more than that of LPS used as a positive control.

EXAMPLE 3

In Vivo Immunocomplex Removal Test

ICR mice (male; age: 6 weeks) purchased from The Experimental Animal Association, Shizuoka Prefecture, each group consisting of 7 mice distributed so as not to cause significant differences in body weight between groups, were served for the experiment at their age of 7–8 weeks. The polysaccharide was administered to the mice, at a dose of 8 mg/kg, 7 days, 5 days, 3 days, and 1 day before, and the same day on which the measurement was performed. GAG was injected as an immunocomplex though caudal vein on the day of the measurement. Blood was sampled at an prescribed interval to measure the residual content of GAG and to determine the half-time of GAG in blood. Since immunocomplexes are decomposed in the reticuloendothelial system and removed therefrom, the weight of liver and spleen, which are the major reticuloendothelial organs, were also measured. The results are shown in Table 2, in which Group I is the control group, Group II indicates the group to which the polysaccharide was administered on the same day of the measurement, and Groups III, IV, V, and VI indicate those groups to which administration were carried out 1, 3, 5, and 7 days before the measurement.

TABLE 2

| Group | Body weight (g) | Liver (g) | Spleen (mg) | Half-time (min) |
|---|---|---|---|---|
| I | 36.0 ± 2.0 | 1.890 ± 0.256 | 136 ± 14 | 8.04 ± 2.69 |
| II | 36.4 ± 2.1 | 1.925 ± 0.407 | 135 ± 27 | 9.95 ± 3.78 |
| III | 35.3 ± 2.0 | 2.017 ± 0.296 | 169 ± 36 | 9.46 ± 2.53 |
| IV | 36.1 ± 1.0 | 2.012 ± 0.213 | 157 ± 7 | 7.19 ± 2.76 |
| V | 35.9 ± 2.3 | 1.973 ± 0.225 | 132 ± 43 | 6.13 ± 1.79 |
| VI | 36.2 ± 1.9 | 1.808 ± 0.151 | 127 ± 19 | 4.83 ± 1.06* |

*$P < 0.05$

As seen from Table 2, the weight of liver and spleen of the tested mice were not significantly different from those of the control group, except for a slight increase in the groups to which the polysaccharide was administered before 1 and 2 days. The GAG half-time decreased in the order of the Groups II, III, IV, V, and VI. Especially, the significant decrease in the half-time in Group VI mice as compared with the control group demonstrates the high GAG removal capacity of the tested polysaccharide.

EXAMPLE 4

Acute Toxicity Test

The acute toxicity test was carried out on 5 ICR female mice (age 7 weeks). A 19.7 mg/ml solution of the acidic heteropolysaccharide prepared in Example 1 was intraperitoneally injected to the mice at a dose of about 0.4 ml, four times at a 2 hour interval, to achieve the total dose of 1,000 mg/kg.

All mice were confirmed to be alive on the 7th day of the administration without change in their systemic conditions.

Obviously, numerous modifications and variations of the present invention are possible in light of the above teachings. It is therefore to be understood that within the scope of the appended claims, the invention may be practiced otherwise than as specifically described herein.

What is claimed is:

1. A method for removing immunocomplexes from the blood of a patient comprising administering an effective amount of an acidic heteropolysaccharide which is secreted by a callus induced from a plant belonging to the genus Polianthes L. to said patient in need thereof.

2. A method according to claim 1, wherein the acidic heteropolysaccharide comprises arabinose, mannose, glactose, glucuronic acid, and xylose as its structural units with the following sequence, and the following ratio:

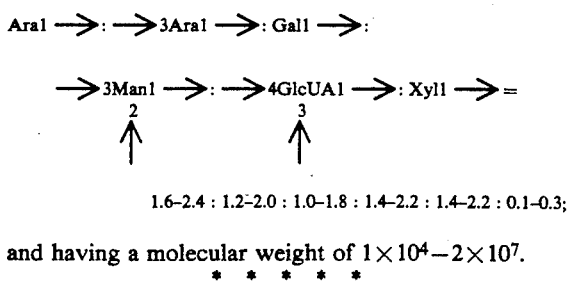

and having a molecular weight of $1 \times 10^4 - 2 \times 10^7$.

* * * * *